United States Patent [19]

Nagato et al.

[11] 4,319,919
[45] Mar. 16, 1982

[54] HERBICIDAL COMPOSITION

[75] Inventors: Shoin Nagato; Nobuo Takagi, both of Tokyo; Heitaro Obara, Shiogama, all of Japan

[73] Assignee: Kaken Chemical Co., Ltd., Tokyo, Japan

[21] Appl. No.: 155,188

[22] Filed: Jun. 2, 1980

[30] Foreign Application Priority Data

Jun. 19, 1979 [JP] Japan ................... 54/76321

[51] Int. Cl.³ ............................ A01N 31/14
[52] U.S. Cl. ........................................ 71/124
[58] Field of Search ........................... 11/124

[56] References Cited

U.S. PATENT DOCUMENTS 2,820,065  1/1958  Slagh ........................... 71/124
3,328,155  6/1967  Walworth ..................... 71/124

FOREIGN PATENT DOCUMENTS 742,623 12/1969 Belgium .
40-29039 12/1965 Japan .
4643112 12/1968 Japan .

OTHER PUBLICATIONS

Nutskii et al., Chem. Abst., vol. 77, (1972), 100575z.
Cullinane et al., J. Chem. Soc., pp. 2942–2947, (1954).

Primary Examiner—Catherine L. Mills
Attorney, Agent, or Firm—Oblon, Fisher, Spivak, McClelland & Maier

[57] ABSTRACT

A herbicidal composition comprises an active ingredient having the formula

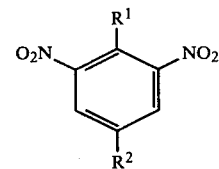

wherein $R^1$ represents a $C_1$–$C_5$ alkoxy group; $R^2$ represents hydrogen atom, or a $C_1$–$C_5$ alkyl group.

7 Claims, No Drawings

HERBICIDAL COMPOSITION

BACKGROUND OF THE INVENTION

The present invention relates to novel herbicidal compositions. More particularly, it relates to herbicidal compositions which have excellent herbicidal effect without phytotoxicity to crop plants such as rice plant, wheat, vegetables, cotton, fruit-tree, soybean and mulberry.

Various herbicidal compositions have been proposed and practically applied. Thus, herbicidal compositions having desired herbicidal effect without phytotoxicity to crop plants have been further required.

SUMMARY OF THE INVENTION

It is an object of the present invention to provide novel herbicidal compositions which have excellent herbicidal effect without phytotoxicity to crop plants especially rice plant wheat, vegetables, cotton, fruit-tree, soybean and mulberry.

It is another object of the present invention to provide herbicidal composition comprising an active ingredient having only one phenyl ring so as to prevent a residual property.

The foregoing and other objects of the present invention have been attained by providing a herbicidal composition comprising an active ingredient having the formula

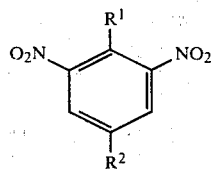

wherein $R^1$ represents a $C_1$–$C_5$ alkoxy group; $R^2$ represents hydrogen atom, or a $C_1$–$C_5$ alkyl group.

DETAILED DESCRIPTION OF THE PREFERRED EMBODIMENTS

The compounds having the formula

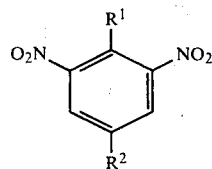

(I)

wherein $R^1$ represents a $C_1$–$C_5$ alkoxy group; $R^2$ represents hydrogen atom, or a $C_1$–$C_5$ alkyl group, can be produced by the process disclosed in Journal of Chemical Society page 2942–2947 (1954).

In the formula (I), $R^1$ is a $C_1$–$C_5$ alkoxy group such as methoxy, ethoxy, propoxy, butoxy or pentoxy group; $R^2$ is H, or a $C_1$–$C_5$ alkyl group such as methyl, ethyl, propyl, butyl or amyl group. The alkyl group in $R^1$ or $R^2$ can be straight or branched chain.

Various compounds having herbicidal activities have been reported. Any herbicidal effect of the compounds having the formula (I) have not been known and the compounds have not been practically utilized.

The herbicidal compositions of the present invention impart excellent selective herbicidal effects to various weeds especially weeds in paddy field such as *Echinochloa crus-galli, Monochoria vaginalis, Ammannia multiflora, Cyperus serotinus, Sagittaria trifolia, Eleocharis kuroguwai, Eleocharis acicularis* and weeds in up-land such as *Digitaria adscendens, Chenopodium album* var. *centrorubrum, Capsella bursa-pastoris, Chenopodium album* or *Amaranthus ascendens.*

The characteristic of the herbicidal composition of the present invention is to have excellent intergeneric selectivity, especially to control gramineous weeds such as *Digitaria adscendens* and *Echinochloa crus-galli* without phytotoxicity to gramineous crop such as rice plant and wheat.

The desired applications are a soil treatment and a water surface treatment. The herbicidal effect of the present invention is especially high in a pre-emergency treatment or a plumule treatment.

One or more compound having the formula (I) can be used as the herbicide in the original form. It is, however, preferable to apply the compound in the form of herbicidal compositions such as wettable powders, emulsifiable concentrates, dusts, granules etc. by admixing with an adjuvant such as various carriers, fillers, solvents, surfactants and stabilizers. It is also possible to combine with the other herbicide, an insecticide, a fungicide, a plant growth regulator etc.

The dose of the active ingredient of the herbicidal composition of the present invention is depending upon a method of the application and a time of the application and usually 10 to 300 g. preferably 20 to 200 g. of the compound (I) per 1 are.

The formulation of the herbicidal composition of the present invention will be further illustrated.

The compounds (I) can be uniformly mixed with or dissolved in suitable adjuvants such as solid carrier such as talc, bentonite, clay, kaolin, diatomaceous earth, silica gel, vermiculite, lime, siliceous sand, ammonium sulfate or urea; liquid carriers such as alcohols, dioxane, acetone, cyclohexanone, methyl naphthalene or dimethylformamide; surfactants as emulsifiers dispersing agents or wetting agents such as alkyl sulfate, alkylsulfonate, polyoxyethyleneglycol ethers, polyoxyethylenealkylaryl ethers such as polyoxyethylenenonylphenol ether or polyoxyethylenesorbitane monoalkylate; and carboxymethyl cellulose, gum arabic and other adjuvants.

| Wettable powder: | |
|---|---|
| Active ingredient: | 5 to 95 wt. % |
| Surfactant: | 1 to 20 wt. % |
| Solid carrier: | 5 to 85 wt. % |

The active ingredient is admixed with the solid carrier and the surfactant and the mixture is pulverized.

| Emulsifiable concentrate: | |
|---|---|
| Active ingredient: | 5 to 95 wt. % |
| Surfactant: | 1 to 40 wt. % |
| Liquid carrier: | 5 to 90 wt. % |

The active ingredient is dissolved in the liquid carrier and the surfactant is admixed.

| Dust: | |
|---|---|
| Active ingredient: | 0.5 to 10 wt. % |

-continued

| Dust: | |
|---|---|
| Solid carrier: | 99.5 to 90 wt. % |

The active ingredient is mixed with fine solid carrier and the mixture is pulverized.

| Granule: | |
|---|---|
| Active ingredient: | 0.5 to 40 wt. % |
| Solid carrier: | 99.5 to 60 wt. % |

Certain examples of the preparations of the herbicidal compositions will be illustrated, however, the kinds and the ratio of the adjuvants are not limited and can be varied from the conventional consideration of the herbicidal compositions.

| Composition 1 (Emulsifiable concentrate): | |
|---|---|
| 2,6-Dinitro-4-t-butylanisole | 20 wt. parts |
| Hexane | 20 wt. parts |
| Xylene | 45 wt. parts |
| Emulsifier (Sorpol 900A: Toho Chem.) | 15 wt. parts |

These components were uniformly mixed to prepare an emulsifiable concentrate. The composition is applied after diluting with water.

| Composition 2 (Wettable powder): | |
|---|---|
| 2,6-Dinitro-4-isopropylanisole | 50 wt. parts |
| Diatomaceous earth | 25 wt. parts |
| Clay | 22 wt. parts |
| Emulsifier (Lunox R-1000-C: Toho Chem.) | 3 wt. parts |

The components were uniformly mixed and pulverized to prepare a wettable powder. The composition is applied after diluting with water.

| Composition 3 (Granule): | |
|---|---|
| 2,6-Dinitro-4-t-butylanisole | 10 wt. parts |
| Bentonite | 30 wt. parts |
| Talc | 55 wt. parts |

The components were uniformly mixed and pulverized and then, kneaded with water and granulated, dried and seived to prepare granules. The composition is applied without a dilution.

EXPERIMENT 1

Herbicidal effect to weeds in paddy field

Each Wagner pot of 1/2000 are was filled with paddy field soil and seeds of *Echinochloa crus-galli* and *Monochloria vaginalis* were sown and stem and root of *Cyperus serotinus* and rice seedling (3 to 4 leaf stage) (Nipponbare) were transplanted and the pot was flooded. Four days after the transplantation, the emulsifiable concentrate of Composition 1 was diluted and applied by a soil treatment at a dose of 100 g. 50 g or 25 g of the active ingredient per 1 are. Forty days after treatment, the herbicidal effects and the phytotoxicities to rice plant were observed and rated as follows. The results are shown in Table 1.

| Herbicidal Effect (percent of Dead weed leaves) | |
|---|---|
| Rate | Percent |
| 0 | less than 4% |
| 1 | 5 to 24% |
| 2 | 25 to 44% |
| 3 | 45 to 69% |
| 4 | 70 to 94% |
| 5 | 95 to 100% |

| Phytotoxicity | |
|---|---|
| − | No damage |
| + | Only slight damage |
| ++ | Slight damage |
| +++ | Middle damage |
| ++++ | Serious damage |
| x | Dead |

As a reference, Benthiocarb emulsifiable concentrate comprising an active ingredient having the formula

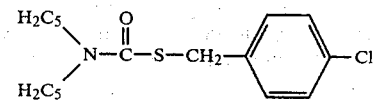

was used.
Note:
E.C. *Echinochloa crus-galli*
M.V. *Monochoria vaginalis*
C.S. *Cyperus serotinus*

TABLE 1

| Active ingredient | Dose of act. ing. (g./are) | Herbicidal effect E.C. | Herbicidal effect M.V. | Herbicidal effect C.S. | Phytotoxicity to rice plant |
|---|---|---|---|---|---|
| 2,6-dinitro-4-t-butyl-anisole | 100 | 5 | 5 | 5 | — |
|  | 50 | 5 | 5 | 5 | — |
|  | 25 | 4–5 | 5 | 4–5 | — |
| 2,6-dinitro-4-iso-propylanisole | 100 | 5 | 5 | 5 | — |
|  | 50 | 4–5 | 4–5 | 4–5 | — |
|  | 25 | 4 | 4 | 5 | — |
| 2,6-dinitro-4-methylanisole | 100 | 5 | 3 | 4 | — |
|  | 50 | 3–4 | 1 | 2–3 | — |
|  | 25 | 3 | 0–1 | 2 | — |
| 2,6-dinitro-4-n-butylanisole | 100 | 5 | 5 | 4 | — |
|  | 50 | 3 | 5 | 3 | — |
|  | 25 | 2 | 4 | 2 | — |
| 2,6-dinitro-4-sec-butylanisole | 100 | 5 | 5 | 3 | — |
|  | 50 | 4–5 | 4–5 | 2–3 | — |
|  | 25 | 4 | 4 | 0–1 | — |
| 2,6-dinitro-4-n-butyl-1-ethoxy-benzene | 100 | 5 | 5 | 4 | — |
|  | 50 | 5 | 4–5 | 3–4 | — |
|  | 25 | 5 | 4–5 | 2 | — |
| 2,6-dinitro-4-sec-butyl-1-ethoxy-benzene | 100 | 5 | 5 | 3 | — |
|  | 50 | 5 | 5 | 2–3 | — |
|  | 25 | 4–5 | 5 | 1 | — |
| 2,6-dinitro-t-butyl-1-ethoxybenzene | 100 | 5 | 5 | 4 | — |
|  | 50 | 5 | 5 | 2–3 | — |
|  | 25 | 5 | 4–5 | 2 | — |
| 2,6-dinitro-4-n-pentyl-1-ethoxy benzene | 100 | 5 | 5 | 3 | — |
|  | 50 | 5 | 4–5 | 2–3 | — |
|  | 25 | 4–5 | 5 | 2 | — |
| 2,6-dinitro-4-t-butyl 1-n-propoxybenzene | 100 | 5 | 5 | 4 | — |
|  | 50 | 5 | 5 | 2–3 | — |
|  | 25 | 5 | 5 | 1 | — |
| 2,6-dinitro-4-n-propyl-n-butoxy-benzene | 100 | 5 | 5 | 4 | — |
|  | 50 | 5 | 5 | 3 | — |
|  | 25 | 4–5 | 4–5 | 2 | — |
| 2,6-dinitro-4-isopro-pyl-1-butoxybenzene | 100 | 5 | 5 | 3 | — |
|  | 50 | 4–5 | 4 | 2–3 | — |
|  | 25 | 4 | 4–5 | 1 | — |
| 2,6-dinitro-4-sec-butyl-1-n-butoxy-benzene | 100 | 5 | 5 | 3–4 | — |
|  | 50 | 5 | 5 | 2–3 | — |
|  | 25 | 5 | 5 | 1 | — |

TABLE 1-continued

| Active ingredient | Dose of act. ing. (g./are) | Herbicidal effect | | | Phytotoxicity to rice plant |
|---|---|---|---|---|---|
| | | E.C. | M.V. | C.S. | |
| 2,6-dinitro-4-t-butyl-1-n-butoxybenzene | 100 | 5 | 5 | 4 | — |
| | 50 | 5 | 5 | 3 | — |
| | 25 | 4–5 | 4–5 | 2 | — |
| 2,6-dinitro-4-n-pentyl-1-n-butoxybenzene | 100 | 5 | 5 | 4 | — |
| | 50 | 5 | 5 | 2–3 | — |
| | 25 | 4–5 | 4–5 | 2 | — |
| 2,6-dinitro-4-methyl-1-n-pentoxybenzene | 100 | 5 | 5 | 3–4 | — |
| | 50 | 4–5 | 5 | 3 | — |
| | 25 | 4–5 | 4–5 | 2 | — |
| Benthiocarb | 50 | 5 | 5 | 5 | +++ |
| | 25 | 5 | 5 | 5 | ++ |
| | 12.5 | 5 | 4 | 4–5 | + |

EXPERIMENT 2

Herbicidal effect to weeds in up-land

Each Wagner pot of 1/2000 are was filled with upland soil and seeds of weeds of *Echinochloa Crus-galli*, *Digitaria adscendens* and *Amaranthus ascendens* and seeds of crops of soybeans, cucumber and wheat were sown in a depth of 1 cm. Next day, each diluted solution of the emulsifiable concentrate of each active ingredient was uniformly sprayed on the soil. Twenty days after the treatment, herbicidal effects and phytotoxicities to crops were observed and rates as those of Experiment 1. The results are shown in Table 2.

Note:
E.C. *Echinochloa crus-galli*
D.A. *Digitaria adscendens*
A.A. *Amaranthus ascendens*
SoB. Soybeans
CuC. Cucumber
Wt. Wheat

TABLE 2

| Active ingredient | Dose of act. ing. (g./are) | Herbicidal effect | | | Phytotoxicity | | |
|---|---|---|---|---|---|---|---|
| | | E.C. | D.A. | A.A. | SoB. | CuC. | Wt. |
| 2,6-dinitro-4-t-butylanisole | 100 | 5 | 5 | 5 | — | — | — |
| | 50 | 5 | 5 | 4 | — | — | — |
| | 25 | 4–5 | 4–5 | 4 | — | — | — |
| 2,6-dinitro-4-isopropylanisole | 100 | 5 | 5 | 5 | — | — | — |
| | 50 | 4–5 | 4–5 | 4 | — | — | — |
| | 25 | 4 | 4 | 3–4 | — | — | — |
| 2,6-dinitro-4-methylanisole | 100 | 5 | 3 | 3 | — | — | — |
| | 50 | 5 | 1 | 2 | — | — | — |
| | 25 | 4 | 0–1 | 1 | — | — | — |
| 2,6-dinitro-4-n-butylanisole | 100 | 4 | 3 | 2 | — | — | — |
| | 50 | 2 | 2 | 1 | — | — | — |
| | 25 | 1 | 0–1 | 0–1 | — | — | — |
| 2,6-dinitro-4-sec-butylanisole | 100 | 5 | 5 | 5 | — | — | — |
| | 50 | 5 | 5 | 4 | — | — | — |
| | 25 | 4–5 | 4–5 | 4 | — | — | — |
| 2,6-dinitro-4-n-butyl-1-ethoxybenzene | 100 | 5 | 5 | 5 | — | — | — |
| | 50 | 5 | 5 | 4 | — | — | — |
| | 25 | 4–5 | 4–5 | 4 | — | — | — |
| 2,6-dinitro-4-sec-butyl-1-ethoxybenzene | 100 | 5 | 5 | 5 | — | — | — |
| | 50 | 5 | 4–5 | 4 | — | — | — |
| | 25 | 4–5 | 4 | 3–4 | — | — | — |
| 2,6-dinitro-t-butyl-ethoxybenzene | 100 | 5 | 5 | 5 | — | — | — |
| | 50 | 5 | 5 | 4 | — | — | — |
| | 25 | 5 | 4–5 | 2 | — | — | — |
| 2,6-dinitro-4-n-pentyl-1-ethoxybenzene | 100 | 5 | 5 | 5 | — | — | — |
| | 50 | 5 | 5 | 4–5 | — | — | — |
| | 25 | 4 | 4 | 3–4 | — | — | — |
| 2,6-dinitro-4-t-butyl-1-n-propoxybenzene | 100 | 5 | 5 | 5 | — | — | — |
| | 50 | 5 | 5 | 3 | — | — | — |
| | 25 | 5 | 4–5 | 2 | — | — | — |
| 2,6-dinitro-4-n-propyl-n-butoxybenzene | 100 | 5 | 5 | 5 | — | — | — |
| | 50 | 4–5 | 4–5 | 4 | — | — | — |
| | 25 | 4 | 4–5 | 4 | — | — | — |
| 2,6-dinitro-4-isopropyl-1-n-butoxybenzene | 100 | 5 | 5 | 5 | — | — | — |
| | 50 | 5 | 5 | 4 | — | — | — |
| | 25 | 4–5 | 4–5 | 4 | — | — | — |
| 2,6-dinitro-4-sec-butyl-1-butoxybenzene | 100 | 5 | 5 | 5 | — | — | — |
| | 50 | 5 | 4–5 | 4 | — | — | — |
| | 25 | 4–5 | 4 | 3–4 | — | — | — |
| 2,6-dinitro-4-t-butyl-1-n-butoxybenzene | 100 | 5 | 5 | 5 | — | — | — |
| | 50 | 4–5 | 4–5 | 4–5 | — | — | — |
| | 25 | 4 | 4 | 4 | — | — | — |
| 2,6-dinitro-4-n-pentyl-1-butoxybenzene | 100 | 5 | 5 | 5 | — | — | — |
| | 50 | 5 | 5 | 4–5 | — | — | — |
| | 25 | 4–5 | 4–5 | 4 | — | — | — |
| 2,6-dinitro-4-methyl-1-n-pentoxybenzene | 100 | 5 | 5 | 5 | — | — | — |
| | 50 | 5 | 5 | 4–5 | — | — | — |
| | 25 | 4–5 | 4–5 | 4 | — | — | — |
| 2,4-dichlorophenyl-4-nitrophenyl-ether | 25 | 4–5 | 5 | 5 | + | ++ | +++ |
| | 12.5 | 4 | 4 | 4 | + | + | + |

PREPARATION 1

2,6-Dinitro-4-t-butyl-1-n-propoxybenzene

Into 70 ml. of ethanol (absolute), 0.92 g. of sodium metal was dissolved and 6.0 g. (0.04 M) of 4-tert-butyl-phenol was added and then, 3.5 g. (0.044 M) of n-propylchloride was added. The mixture was refluxed for 20 hours and ethanol was distilled off and water was added. The reaction product was extracted with benzene and benzene layer was washed with 3% NaOH aqueous solution and with water and dehydrated over sodium sulfate and then, benzene was distilled off and a residue was distilled under a reduced pressure to obtain 4-tert-butyl-1-n-propoxybenzene. The product was dissolved into 6 ml. of glacial acetic acid and then, 12 ml. of fuming nitric acid (d=1.5) was added at 0° to 5° C. to react them for 1 hour and then, the reaction was continued at the ambient temperature for 1 hour at 35° to 40° C. for 4 hours. The reaction mixture was poured into ice water and the product was extracted with chloroform and washed with water, with 3% Na$_2$CO$_3$ aqueous solution and with water and dehydrated over sodium sulfate and chloroform was distilled off and the residue was recrystallized from ethanol to obtain 4.5 g. (43%) of a pale yellow crystal. (melting point of 106° to 107° C.)

PREPARATION 2

2,6-Dinitro-4-n-propyl-1-n-butoxybenzene

Into 70 ml. of ethanol (absolute), 1.15 g. of sodium metal was dissolved and 6.8 g. (0.05 M) of 4-n-propyl-phenol was added and then, 11.0 g. (0.1 M) of n-butyl-bromide was added. The mixture was refluxed for 20 hours and ethanol was distilled off under a reduced pressure and water was added. The product was extracted with benzene and washed with 3% NaOH aqueous solution and with water and dehydrated over sodium sulfate and benzene was distilled and the residue was distilled under a reduced pressure to obtain 4-n-propyl-n-butoxybenzene. In 5 ml. of glacial acetic acid, 5.5 g. (0.025 g.) of 4-n-propyl-n-butoxybenzene was dissolved and 10 ml. of fuming nitric acid (d=1.5) was added and then, 10 ml. of 20% fuming sulfuric acid was added to react them at 0° to 5° C. for 1 hour, and then at a room temperature for 1 hour and at 35° to 40° C. for 4 hours. The reaction mixture was poured into ice water and the product was extracted with chloroform and the chloroform layer was washed with water, with 3% Na$_2$CO$_3$ aqueous solution and with water and dehydrated over sodium sulfate and chloroform was distilled off and the residue was distilled off under a reduced pressure to obtain 1.6 g. (yield of 20.6%) of 2,6-dinitro-4-n-propyl-1-n-butoxybenzene. (boiling point of 170° to 172° C./1.5 mmHg).

We claim:

1. A method of controlling the growth of weeds, comprising:

applying to said weeds a herbicidally effective amount of a composition comprising, as the active ingredient, a compound of the formula:

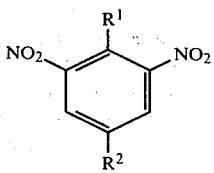

wherein R$^1$ is C$_1$–C$_5$ alkoxy, and R$^2$ is hydrogen or C$_1$–C$_5$ alkyl in combination with a herbicidal adjuvant.

2. A method of controlling the growth of weeds, comprising:

applying a herbicidally effective amount of a composition comprising, as the active ingredient, a compound of the formula:

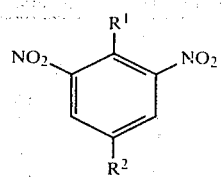

wherein R$^1$ is C$_1$–C$_5$ alkoxy, and R$^2$ is hydrogen or C$_1$–C$_5$ alkyl in combination with a herbicidal adjuvant to the soil during the preemergent stage of growth of said weeds.

3. The method of claim 1 or 2, wherein said composition is applied in an amount of 10–300 grams of said active ingredient per one are.

4. The method of claim 3, wherein said composition is applied in a quantity of 20–200 grams of said active ingredient per one are.

5. The method of claim 1 or 2, wherein said composition is in the form of a formulation selected from the group consisting of (a) 5–95 weight percent of said active ingredient, 1–20 weight percent of a surfactant and 5–85 weight percent of a solid carrier in the form of a wettable powder, (b) 5–95 weight percent of said active ingredient, 1–40 weight percent of a surfactant and 5–90 weight percent of a liquid carrier in the form of an emulsufiable concentrate, (c) 0.5–10 weight percent of said active ingredient and 99.5–90 weight percent of a solid carrier in the form of a dust, and (d) 0.5–40 weight percent of said active ingredient and 99.5–60 weight percent of a solid carrier in granular form.

6. The method of claim 1 or 2, wherein said adjuvant is a solid carrier selected from the group consisting of talc, bentonite, clay, kaolin, diatomaceous earth, silica gel, vermiculite, lime, siliceous sand, ammonium sulfate and urea; a liquid carrier selected from the group consisting of alcohols, dioxane, acetone, cyclohexanone, methylnaphthalene and dimethylformamide; a surfactant selected from the group consisting of an alkyl sulfate, an alkyl sulfonate, a polyoxyethylene glycol ether, a polyoxyethylene glycol ether, a polyoxyethylene alkyl aryl ether, and a polyoxyethylenesorbitane monoalkylate; carboxymethylcellulose; or gum arabic.

7. The method of claim 1 or 2, wherein said composition is in the form of a wettable powder, an emulsifiable concentrate, a dust, or a granular material.

* * * * *